US011104933B1

(12) United States Patent
Fleischman et al.

(10) Patent No.: US 11,104,933 B1
(45) Date of Patent: Aug. 31, 2021

(54) COMPOSITIONS AND METHODS FOR DETERMINING THE PRESENCE OF ACTIVE LEUKOCYTE CELLS USING AN ELECTROCHEMICAL ASSAY

(71) Applicant: Cleu Diagnostics, LLC, Philadelphia, PA (US)

(72) Inventors: Andrew Neil Fleischman, Longport, NJ (US); Javad Parvizi, Gladwyne, PA (US); Ron H. Bihovsky, Wynnewood, PA (US)

(73) Assignee: CLEU DIAGNOSTICS, LLC, Philadelphia, PA (US)

( * ) Notice: Subject to any disclaimer, the term of this patent is extended or adjusted under 35 U.S.C. 154(b) by 129 days.

(21) Appl. No.: 16/145,014

(22) Filed: Sep. 27, 2018

Related U.S. Application Data

(63) Continuation-in-part of application No. 16/087,411, filed as application No. PCT/US2017/022976 on Mar. 17, 2017.

(60) Provisional application No. 62/352,560, filed on Jun. 21, 2016, provisional application No. 62/311,405, filed on Mar. 22, 2016.

(51) Int. Cl.
*C12Q 1/44* (2006.01)
*C07D 213/79* (2006.01)
*G01N 33/487* (2006.01)

(52) U.S. Cl.
CPC ............ *C12Q 1/44* (2013.01); *C07D 213/79* (2013.01); *G01N 33/48721* (2013.01); *G01N 2800/26* (2013.01); *G01N 2800/50* (2013.01)

(58) Field of Classification Search
None
See application file for complete search history.

(56) References Cited

U.S. PATENT DOCUMENTS

| 4,278,763 | A | * | 7/1981 | Berger ............... C12Q 1/37 435/23 |
| 4,299,917 | A | | 11/1981 | Berger et al. |
| 4,637,979 | A | | 1/1987 | Skjold et al. |
| 4,657,855 | A | | 4/1987 | Corey et al. |
| 4,677,060 | A | | 6/1987 | Valet |
| 4,897,444 | A | | 1/1990 | Brynes et al. |
| 5,464,739 | A | | 11/1995 | Johnson |
| 5,512,450 | A | | 4/1996 | Johnson et al. |
| 5,574,323 | A | | 11/1996 | Nusser |
| 5,663,044 | A | | 9/1997 | Noffsinger |
| 6,503,725 | B2 | | 1/2003 | Huh |
| 6,528,652 | B1 | | 3/2003 | Huh |
| 7,935,538 | B2 | | 5/2011 | Song et al. |
| 9,194,807 | B2 | | 11/2015 | Song |
| 2003/0207264 | A1 | | 11/2003 | Packard et al. |
| 2004/0175296 | A1 | | 9/2004 | Opalsky |
| 2009/0181416 | A1 | | 7/2009 | Song |
| 2009/0258348 | A1 | | 10/2009 | Sprinzl |
| 2010/0226931 | A1 | | 9/2010 | Valiante et al. |
| 2014/0329254 | A1 | | 11/2014 | Yang |
| 2016/0040209 | A1 | | 2/2016 | Zhang et al. |
| 2017/0037450 | A1 | | 2/2017 | Zourob |
| 2018/0179090 | A1 | * | 6/2018 | Liu ............... B09C 1/002 |
| 2019/0064164 | A1 | | 2/2019 | Lakshmipathy |

FOREIGN PATENT DOCUMENTS

| DE | 19829707 | | 1/2000 | |
| EP | 0698600 | | 2/1996 | |
| JP | H03244396 | | 10/1991 | |
| JP | H0867651 | | 3/1996 | |
| JP | H08220090 | | 8/1996 | |
| KR | 1020150129908 | | 11/2015 | |
| WO | 03043583 | | 5/2003 | |
| WO | 2009074891 | A2 | 6/2009 | |
| WO | 2009089680 | | 7/2009 | |
| WO | 2010022281 | A1 | 2/2010 | |
| WO | 2010036930 | A1 | 4/2010 | |
| WO | 2010151878 | A2 | 12/2010 | |
| WO | 2013112216 | A1 | 8/2013 | |
| WO | 2014165618 | A1 | 10/2014 | |
| WO | WO-2015184442 | A1 * | 12/2015 | ............... C07H 3/04 |
| WO | 2017165222 | | 9/2017 | |
| WO | 2019094575 | | 5/2019 | |

OTHER PUBLICATIONS

Nagy et al. Biosensors and Bioelectronics (2000) 15: 265-272 (Year: 2000).*
Defintion of monoester downloaded from https://www.merriam-webster.com/dictionary/monoester on Jul. 19, 2020 (Year: 2020).*
Definition of "depict" downloaded from http:www//merriam-webster.com.defintion/depict on Jan. 15, 2019 (Year: 2019).
Goddard et al. Trends Biotechnol. (2004) 22(7): 363-370 (Year: 2004).
Harris et al. Proc. Natl Acad. Sci (2005) 97(14): 7754-7759 (Year: 2005).
Translation of KR 1020150129908 downloaded from http://engpat.kipris.or.kr/pmt/patent/getTransRes.do?commKey=null&AN=1020140056480 on Jan. 9, 2019; published Nov. 23, 2015 (Year: 2015).
Supplementary European Search Report dated Dec. 6, 2019 in European Application No. 17770862.5.
Wolfgang Schoenfelder et al., "Synthese von mehrfach homochiral-analog substituierten Benzolderivaten," Chemische Berichte, Jan. 1, 1980, XP055057858 [retrieved on Mar. 26, 2013], pp. 1855-1866.
Seong Ryong Nam et al., "Control of Macroscopic Helicity by Using the Sergeant-and-Soldiers Principle in Organogels," Chemistry—A European Journal, vol. 14, No. 20, Jul. 7, 2008, pp. 6040-6043.
Vicente Marti-Centelles et al., "Zinc(ii) corrdination polymers with psydopeptidic ligands," CrystEngComm, vol. 13, No. 23, Jan. 1, 2011, pp. 6997-7008.
Database Calpus [Online] Chemical Abstracts Service, Funama, Jun-Ichi et al., "Enkephalin dimers cross-linked by diaminobenzene for homodimeric opoid receptors expressed in COS-7 Cells," XP002795738, retrieved from STN Database accession No. 2006:506020, Peptide Science, Protein Search Foundation, Minn, JP, vol. 2005/42nd, Jan. 1, 2006, pp. 211-212.

(Continued)

Primary Examiner — Susan M Hanley
(74) Attorney, Agent, or Firm — FisherBroyles LLP

(57) ABSTRACT

The present disclosure relates to compositions, methods and test devices for determining the presence of active leukocyte cells, for example, by using novel LE and/or HNE substrates in an electrochemical assay.

8 Claims, 7 Drawing Sheets

(56) References Cited

OTHER PUBLICATIONS

International Search Report for International Application No. PCT/US2017/022976 dated Jul. 19, 2017.
Written Opinion of the International Searching Authority for International Application No. PCT/US2017/022976 dated Jul. 19, 2017.
Males BM, Bartholomew WR, Amsterdam D. Leukocyte esterase-nitrite and bioluminescence assays as urine screens. Journal of Clinical Microbiology. 1985;22(4):531-534.
Fraser PA, Teasdale J, Gan KS, Eglin R, Scott SC, Lacey CJ. Neutrophil enzymes in urine for the detection of urethral infection in men. Genitourin Med. 1995;71(3):176-179.
Korkmaz B, Attucci S, Epinette C, Pitois E, Jourdan ML, Juliano L, Gauthier F. Measurement of neutrophil elastase, proteinase 3, and cathepsin G activities using intramolecularly quenched fluorogenic substrates. Methods Mol Biol. 2012;844:125-38.
Schulenburg C, Faccio G, Jankowska D, Maniura-Weber K, Richter M. A FRET-based biosensor for the detection of neutrophil elastase. Analyst. Mar. 7, 2016;141(5):1645-8.
Aggarwal VK, Tischler E, Ghanem E, Parvizi J. Leukocyte esterase from synovial fluid aspirate: A technical note. J Arthroplasty. 2013;28(1):193-195.
Tischler EH, Cavanaugh PK, Parvizi J. Leukocyte esterase strip test: Matched for musculoskeletal infection society criteria. J Bone Joint Surg Am. 2014;96(22):1917-1920.
Deirmengian C, Kardos K, Kilmartin P, et al. The alpha-defensin test for periprosthetic joint infection outperforms the leukocyte esterase test strip. Clin Orthop Relat Res. 2015;473(1):198-203.
Murthy VV, Karmen A. A simple spectrophotometric assay for urinary leukocyte esterase activity. Biochem Med Metab Biol. 1988;40(3):260-268.
Parvizi J, Walinchus L, Adeli B. Molecular diagnostics in periprosthetic joint infection Int J Artif Organs. Sep. 2011; 34(9):847-55.
Parvizi J, Jacovides C, Antoci V, Ghanem E. Diagnosis of periprosthetic joint infection: the utility of a simple yet unappreciated enzyme. J Bone Joint Surg Am. Dec. 21, 2011; 93(24):2242-8.
Hanson et al "Electrochemical Substrate and Assay for Esterolytic Activity of Human White Blood Cells," Analyitical Chemistry, Jun. 13, 2017, vol. 89, pp. 77881-7787.
International Search Report dated Feb. 11, 2020 for International Application No. PCT/US2019/053224.
Mahajan et al., "Juvenile hormone like substances: Part XV—Synthesis and biological activities of some juvenile analogues containing sulphonamide feature." Indian Journal of Chemistry—Section B Organic and Medicinal Chemistry, Dec. 2002, vol. 41B, pp. 2635-2641.
Written Opinion of the International Searching Authority dated Feb. 11, 2020 for International Application No. PCT/US2019/053224.
Hanson et al., "Synthesis and Characterization of Pyridine Compounds for Amperometric Measurements of Leukocyte Esterase," Chembiochem, vol. 19, Issue 14, Apr. 20, 2018.
Definition of "substitutive" downloaded from https://www.marriam-webster.com/dictionary/substitutive on May 5, 2020 (Year:2020).
European Office Action dated Apr. 8, 2021 in European Application No. 17 770 862.5.
Japanese Office Action dated Apr. 27, 2021 in Japanese Application No. 2019-500736, including English translation.

\* cited by examiner

COMPOSITIONS AND METHODS FOR DETERMINING THE PRESENCE OF ACTIVE LEUKOCYTE CELLS USING AN ELECTROCHEMICAL ASSAY

I. CROSS-REFERENCE TO RELATED APPLICATIONS

This application is a continuation-in-part of application Ser. No. 16/087,411, filed Sep. 21, 2018, a national stage application of International Application Number PCT/US2017/022976, which claims priority to U.S. Provisional Patent Application Ser. No. 62/311,405, filed Mar. 22, 2016, and to U.S. Provisional Patent Application Ser. No. 62/352,560, filed Jun. 21, 2016. The disclosure of each of the applications identified above are hereby incorporated by reference in their entirety.

II. FIELD OF THE INVENTION

The present disclosure relates to a novel application of an electrochemical assay for the determination of the activity of leukocyte cells within a test sample. More particularly, the present disclosure relates to novel methods and kits for determining the activity of enzymes released by active leukocyte cells, especially leukocyte esterase and human neutrophil elastase, in a patient at risk of developing an infection.

III. BACKGROUND OF THE INVENTION

The presence of an abnormally high number of leukocyte cells in urine is a commonly used indicator of an infectious process. Historically, technicians have relied on manual visual count under a microscope. This visual technique has been largely replaced by a dipstick assay for detection of urogenital infections. In a large majority of such commercial 'dipstick' assays, activity of the enzyme leukocyte esterase ("LE") is used as a proxy for the presence of active leukocyte cells. An assay for human neutrophil elastase ("HNE") has also been reported to have great sensitivity for the diagnosis of urethral infections in men.

Known assays for LE are chromogenic, in that the presence of enzyme activity is reported based upon a color change. Typically, a color test strip can be matched to a color chart with 3-4 increments of increasing color intensity (from none to 2+/3+), which represents a LE concentration of 30 ng/mL to greater than 1500 ng/mL. However, there are clear disadvantages to a colorimetric assay. With only 3-4 available color intensity increments, resolution of differences in leukocyte esterase concentration may be quite difficult. In addition, inter-rater and even intra-rater reliability in classifying such color increments may be poor. This is especially true for instances in which dipstick results are less definitive (truce or 1+); test results, in such cases, may be too unreliable for making treatment decisions. Thus, the utility of dipstick results is limited to cases in which leukocyte esterase activity is exceedingly high. Any substance that changes the color of urine (e.g. nitrofurantoin, phenazopyridine) also affects dipstick readings.

In recent years, leukocyte esterase testing has piqued the interest of physicians for applications using serous fluid, such as that from joint, lung, abdominal, or even middle ear effusions. While results have been quite promising for the diagnosis of periprosthetic joint infection (PJI), a colorimetric test is rendered impractical in as many as 17-29% of samples due to the presence of blood or debris. The same would be true for other body cavities, for which aspiration often does not yet often always yield clear fluid. Further, a colorimetric leukocyte esterase test cannot be attempted on serum samples.

More recently, a lactate ester substrate has been demonstrated to have improvement in terms of LE assay sensitivity and speed. The alcohol portion is released as a hydroxylpyrrole compound, which then reacts with diazonium salt to produce a purple azo dye. However, such an assay has limited utility in bloody or turbid fluid conditions and would require expensive optical sensors to provide a precise, quantitative measurement. Accordingly, there is an urgent need for improved substrates and assays to detect leukocytes and leukocyte enzymes in a sample.

IV. SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

In one aspect, the disclosure is directed towards a method for screening, detecting and confirming an infection in patients at risk of an infection or those patients who have already exhibited symptoms associated with an infection. In one embodiment, the method follows the step of obtaining a sample from the subject in need, detecting the presence or absence of leukocyte markers in the sample, and instituting a therapeutic regimen based on the degree and presence of the leukocyte markers in the sample.

In some embodiments, the leukocyte markers can be one or any combinations of such markers as cytokines, chemokines, oxygen and nitrogen radicals, leukocyte elastase, leukocyte esterase, neutrophil elastase, gelatinases, IL-1β, metalloproteinases (MMPs), cathepsins, such as cathepsin A and cathepsin B, phospholipases, such as, for example, phospholipase A and phospholipase B.

In one aspect, the present disclosure is directed to a composition comprising a leukocyte enzyme or specifically a neutrophil enzyme substrate. In some embodiments, the leukocyte enzyme comprises leukocyte esterase ("LE"). In some embodiments, the leukocyte enzyme substrate comprises an LE substrate. In some embodiments, the leukocyte enzyme comprises human neutrophil elastase ("HNE"). In some embodiments, the leukocyte enzyme substrate comprises an HNE substrate. In an alternative embodiment, the composition comprises both an LE substrate and a HNE substrate. In yet another embodiment, the composition may contain additional substrates specific to other enzymes or biomarkers than LE and HNE.

In some embodiments, the substrates demonstrate specificity for LE or HNE. In one embodiment, the substrate comprises a monoester, the monoester being one of an α-amino acid ester, such as an alanine ester, or an α-hydroxy acid ester, such as a lactate ester, with specificity for leukocyte esterases, the monoester having a first moiety for participating in a redox reaction, and a second moiety comprising an amine or alcohol blocking group, which masks the functional group (i.e., amine or alcohol) to prevent undesirable chemical reactivity.

In some embodiments, the substrates may follow Formula I as depicted below:

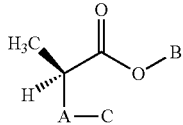

Formula I wherein A comprises an ether group (i.e. —O—) or an amine group (i.e., NR$^a$, where R$^a$ is a H or an optionally substituted alkyl, aryl, or aralkyl group), B comprises a moiety capable of participating in a redox reaction, and C comprises an alcohol or amine blocking group. In some embodiments, A comprises an amino group. In some embodiments, A comprises an ether group. In some embodiments, B comprises a redox active alcohol intermediate. In some embodiments, B comprises a phenol. In some embodiments, B comprises a substituted phenol. In some embodiments, C comprises a tosyl protecting group. In some embodiments, the oxygen linking B in Formula I is substituted with an amino group. In further embodiments, B comprises aminophenyl. In some embodiments, B comprises a substituted aminophenyl.

In some embodiments, the LE substrate comprises a compound as described in Formula II below:

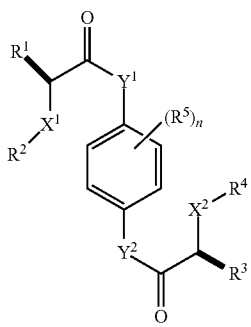

Formula II

X1 and X2 are independently O, S or NRa. Ra is an H, an alkyl or an aryl group. X1 and X2 can be both oxygen or both NRa. Alternatively, one of X1 and X2 is oxygen and the other is NRa.

Y1 and Y2 are independently O or NRa. Ra is as described above. Y1 and Y2 can be both oxygen or both NRa. Alternatively, one of Y1 and Y2 is oxygen and the other is NRa.

R1 and R2 are independently an alkyl or an aryl group or a substituted alkyl, a substituted aryl or a protecting group. In some embodiments, R1 and R2 are both methyl. In some embodiments, R1 and R2 may be a tosyl. In some embodiments, R2 may be a tosyl.

R3 and R4 are independently an alkyl, a protecting group or a peptide moiety. Example of a protecting group includes tosyl, benzoyl, benzyl, trimethylsilyl, [bis-(4-methoxyphenyl)phenylmethyl], carbobenzyloxy, and tert-Butyloxycarbonyl, 9-Fluorenylmethyloxycarbonyl. In one embodiment, R4 may be a tosyl. The peptide moiety can include any combination of natural and/or non-natural amino acids.

Each of the R5 on the ring is independently a halogen atom; a hydroxyl group; a C1-C6 alkyl group; a C3-C6 cycloalkyl group; C3-C6 cycloalkyl C1-C6 alkyl group; a C2-C6 alkenyl group; a C2-C6 alkynyl group; a C1-C6 haloalkyl group (including trifluoro C1-C6 alkyl); a C2-C6 haloalkenyl group; a C2-C6 haloalkynyl group; a C3-C6 halocycloalkyl group; a C3-C6 halocycloalkyl C1-C6 alkyl group; a C1-C6 alkoxy group; a C3-C6 cycloalkyloxy group; a C2-C6 alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ alkylcarbonylamino group; a mono($C_1$-$C_6$ alkyl)amino group; a di($C_1$-$C_6$ alkyl)amino group; a hydroxy $C_1$-$C_6$ alkyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a cyano $C_1$-$C_6$ alkyl group; a $C_1$-$C_6$ alkoxy $C_1$-$C_6$ alkoxy group; a $C_3$-$C_6$ cycloalkyl $C_1$-$C_6$ alkyloxy group; a $C_1$-$C_6$ haloalkoxy $C_1$-$C_6$ alkoxy group; a cyano $C_1$-$C_6$, alkoxy group; a $C_1$-$C_6$ acyl group; a $C_1$-$C_6$ alkoxyimino $C_1$-$C_6$ alkyl group; a carboxyl group; a $C_1$-$C_6$ alkoxycarbonyl group; a carbamoyl group; a mono ($C_1$-$C_6$ alkyl)aminocarbonyl group; a di($C_1$-$C_6$ alkyl)aminocarbonyl group; a nitro group; or a cyano group. n is 0, 1, 2, 3, or 4.

In some embodiments, the LE substrate comprises 4-((tosyl-L-alanyl)oxy)phenyl tosyl-L-alaninate. In some embodiments, the LE substrate comprises 4-(((S)-2-(tosyloxy)propanoyl)oxy)phenyl (S)-2-(tosyloxy)propanoate. In some embodiments, the LE substrate comprises a phenylenediamine variant of one of 4-((tosyl-L-alanyl)oxy)phenyl tosyl-L-alaninate and 4-(((S)-2-(tosyloxy)propanoyl)oxy)phenyl (S)-2-(tosyloxy)propanoate.

In some embodiments, the HNE substrate comprises a compound as described in Formula III below:

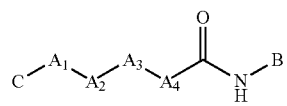

Formula III wherein $A_1$-$A_2$-$A_3$-$A_4$ represent a core tetrapeptide scaffold sequence which serves as the enzyme active site, B comprises a moiety capable of participating in a redox reaction, and C comprises an acyl group. In some embodiments, $A_1$-$A_2$-$A_3$-$A_4$ comprise AAPV (SEQ ID NO: 1). In some embodiments, SEQ ID NO: 1 has conservative substitutions. In some embodiments, B comprises a redox active alcohol intermediate. In some embodiments, B comprises a derivative of phenol. B comprises a quinone. In some embodiments, B comprises a hydroquinone. In some embodiments, B comprises a substituted quinone or a substituted hydroquinone. In some embodiments, C comprises N-methyoxysuccinyl.

In some embodiments, the HNE substrate comprises 3-{[(1S)-1-{[(2S)-1-(5-{[(1S)-1-({4-[(2S)-2-({1-[(2S)-2-[(2S)-2-(3-carboxypropanamido)propanamido]propanoyl] pyrrolidin-2-yl}formamido)-3-methylbutanamido] phenyl}carbamoyl)-2-methylpropyl] carbamoyl}imidazolidin-1-yl)-1-oxopropan-2-yl] carbamoyl}ethyl]carbamoyl}propanoic acid.

In some embodiments, the leukocyte enzyme substrate is included in an assay. In some embodiments, the assay comprises an electrochemical assay. In an alternative embodiment, the assay may include a colorimetric step in combination with the electrochemical assay. In some embodiments, the electrochemical assay comprises an internally calibrated electrochemical continuous enzyme assay ("ICECEA"). In some embodiments, the electrochemical assay comprises a leukocyte substrate of the present disclosure and an electrochemical measuring device. In some embodiments, the electrochemical measuring device includes a working electrode, a reference electrode, and an auxiliary electrode.

In some embodiments, the present disclosure is directed to a method of detecting the presence of a leukocyte enzyme in a sample and instituting a therapeutic plan. In some embodiments, the presence of a leukocyte enzyme in the sample indicates the presence of a leukocyte in the sample. In some embodiments, the leukocyte enzyme comprises LE. In some embodiments, the leukocyte enzyme comprises human neutrophil elastase HNE. In some embodiments, the leukocyte enzyme is detected by contacting the enzyme with a substrate of the enzyme. In some embodiments, the substrate is any LE substrate of the present disclosure. In some embodiments, the substrate is any HNE substrate of the present disclosure.

In some embodiments, the amount of leukocyte enzyme present in the sample is quantified. In some embodiments, the presence of a leukocyte in the sample is indicative of an infection. In some embodiments, the infection comprises a urinary tract infection ("UTI"). In some embodiments, the infection comprises a periprosthetic joint infection ("PJI"). In some embodiments, the infection comprises spontaneous bacterial peritonitis ("SBP"). In some embodiments, the sample comprises a biological sample. In some embodiments, the biological sample comprises one of urine, sputum, synovial fluid, pleural fluid, pericardial fluid, peritoneal fluid, cerebrospinal fluid ("CSF") and middle ear fluid.

In some embodiments, the method of screening a patient at risk of developing an infection following the steps of detecting the presence of a leukocyte enzyme in a sample by contacting a leukocyte enzyme with a substrate in an assay. In some embodiments, the assay comprises an electrochemical assay. In some embodiments, the electrochemical assay comprises an internally calibrated electrochemical continuous enzyme assay ("ICECEA").

In some embodiments, the method of detecting the presence of a leukocyte enzyme in an electrochemical assay comprises a step of adding a first aliquot of a reactant or product of a leukocyte enzyme to a substrate of the leukocyte enzyme. In some embodiments, the leukocyte enzyme substrate is in an electrolyte solution. In some embodiments, the method comprises a step of measuring current flowing through an electrode of the electrochemical assay. In some embodiments, the method comprises a step of adding at least one additional aliquot of the reactant or product of a leukocyte enzyme to the substrate of the leukocyte enzyme. In some embodiments, the method comprises a step of measuring current flowing through an electrode of the electrochemical assay for a second time. In some embodiments, the method comprises a step of adding the leukocyte enzyme to the substrate of the leukocyte enzyme. In some embodiments, the method comprises a step of measuring current flowing through an electrode of the electrochemical assay for a third time.

In some embodiments, the method of screening a patient for infection by detecting the presence of a leukocyte enzyme in an electrochemical assay following a process including a step of adding a first aliquot of a leukocyte enzyme to a substrate of the leukocyte enzyme. In some embodiments, the leukocyte enzyme substrate is in an electrolyte solution. In some embodiments, the method comprises a step of measuring current flowing through an electrode of the electrochemical assay. In some embodiments, the method comprises a step of adding at least one additional aliquot of the leukocyte enzyme to the substrate of the leukocyte enzyme. In some embodiments, the method comprises a step of measuring current flowing through an electrode of the electrochemical assay for a second time. In some embodiments, the method comprises a step of adding a product or reactant of a leukocyte enzyme to the substrate of the leukocyte enzyme. In some embodiments, the method comprises a step of measuring current flowing through an electrode of the electrochemical assay for a third time.

In another aspect, the present disclosure is directed to kits containing suitable substrate, direction for optimizing the results and optionally providing patient specific therapeutic regimen based on the observed results.

V. BRIEF DESCRIPTION OF THE FIGURES

VI. DETAIL DESCRIPTION OF THE INVENTION

Figure 1:
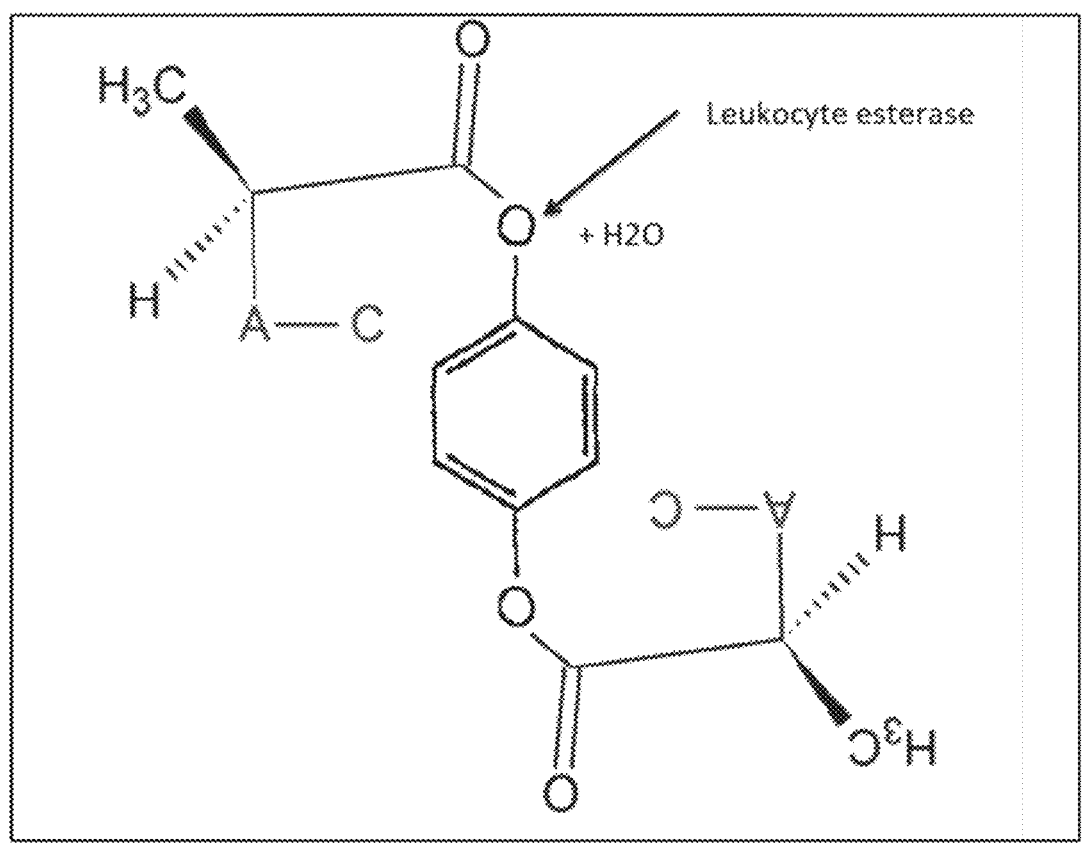
FIG. 1 represents an initial hydroquinone substrate and first ester hydrolysis step.

As used herein and in the appended claims, the singular forms "a", "and" and "the" include plural references unless the context clearly dictates otherwise.

As used herein, "leukocyte" may refer to any white blood cell ("WBC"). Leukocytes are cells of the immune system that are involved in protecting the body against infectious disease and invading pathogens. All leukocytes/WBCs are divided into five classes based on morphological characteristics that differentiate themselves from one another. They include neutrophils, eosinophils, basophils, monocytes, and lymphocytes. Neutrophils comprise approximately 40-75% of leukocytes, eosinophils comprise approximately 1-6% of leukocytes, basophils comprise less than 1% of leukocytes, monocytes comprise approximately 2-10% of leukocytes, and lymphocytes (e.g. B lymphocytes and T lymphocytes) comprise approximately 20-45% of leukocytes.

The term "patient" as used herein may refer to a biological system to which a treatment can be administered. A biological system can include, for example, an individual cell, a set of cells (e.g. a cell culture), an organ, a tissue, or multicellular organism. A "patient" can refer to a human patient or a non-human patient. In preferred embodiments, the patient is a human patient.

The terms "effective amount" or "therapeutically effective amount" as used herein may refer to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder.

The present disclosure relates to compositions and methods for rapid detection (including determining the relative activity) of enzymes released by active leukocyte cells, e.g. leukocyte enzymes released by active leukocyte cells, in particular leukocyte esterase ("LE") and human neutrophil elastase ("HNE").

In at least one aspect of the present disclosure, a method of screening a subject for infection is described, the method comprising the steps of (a) obtaining a sample of tissue or bodily fluid from a subject at risk of developing an infection, (b) applying the sample to a detector device, wherein the detector device comprises at least one substrate which is specific for at least one of LE and/or HNE, wherein at least one substrate is adapted to detect a threshold level at least one of LE and/or HNE, the threshold level correlated with a presence of infection; (c) ascertaining the threshold levels of LE and/or HNE present in the sample, wherein if the concentration each of LE and/or HNE exceeds the threshold level, and further wherein such measurement is a positive screen for infection.

The disclosure provides a method wherein the infection is a periprosthetic joint infection (PJI). In some embodiments, the threshold level of leukocyte esterase (LE) for detection of PJI is at least about 20 pg/m of leukocyte esterase in a synovial fluid sample.

The compositions and methods for rapid detection utilize specific substrates for detecting leukocyte enzymes, e.g. LE and HNE, referred to as LE substrates and HNE substrates respectively. The compositions and methods for rapid detection may utilize electrochemical assays to detect the leukocyte enzymes, in particular, internally calibrated electrochemical continuous enzyme assay ("ICECEA"), but are not necessarily limited as such.

In some embodiments, the substrates are capable of detecting LE. Such substrates are readily hydrolyzed by LE to generate a redox intermediate, which can provide a detectable electrochemical response. In some embodiments, the substrates for detecting LE (i.e. "LE substrates") may follow Formula I as depicted below:

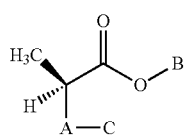

Formula I

Where A determines the identity of the acyl group, e.g. an alanine or lactate, at the ester cleavage site with enzyme specificity for leukocyte esterase and B is a moiety capable of participating in a redox reaction, which can be detected using an electrochemical assay (e.g. by using ICECEA or screen-printed electrochemical sensors).

In some embodiments, A comprises an amino group (i.e., —NR$^a$, where R$^a$ is a H or an optionally substituted alkyl, aryl, or aralkyl group), or A comprises an ether group (i.e. —O—).

The acyl group defined by A is protected using any effective amine or alcohol blocking group C (e.g. a tosyl group). The alcohol intermediate of the ester, moiety B, to be released upon hydrolysis by the esterase is a redox substrate and participates in a redox reaction. Additionally, the oxygen linking B in Formula I may be substituted with an —NH linking moiety (i.e. the ester group presented in Formula I may be substituted with an amido group) and still be within the scope of the present disclosure.

The amine or alcohol blocking group C may comprise any of the following: acetyl (Ac), benzoyl (Bz), benzyl (Bn), β-methoxyethoxymethyl (MEM), dimethoxytrityl (DMT), methyoxymethyl (MOM), methoxytrityl [(4-methoxyphenyl)diphenylmethyl](MMT), p-Methoxybenzyl (PMB), methylthiomethyl, pivaloyl (Piv), tetrahydropyranyl (THP), tetrahydrofuran (THF), trityl (Tr), sily (e.g. TMS, TBDMS, TOM, TIPS), methyl, and ethoxyethyl (EE), benzyloxycarbonyl (Cbz); p-methoxybenzylcarbonyl (Moz or MeOZ), tert-butoxycarbonyl (BOC), 9-fluorenylmethyloxycarbonyl (FMOC), 3,4-Dimethoxybenzyl (DMPM), p-methoxyphenyl (PMP), tosyl (Ts), trichloroethoxycarbonyl (Troc), arylsulfonyl, or alkylsulfonyl (e.g. Nosyl and Nps[MOU1]).

Figure 2:
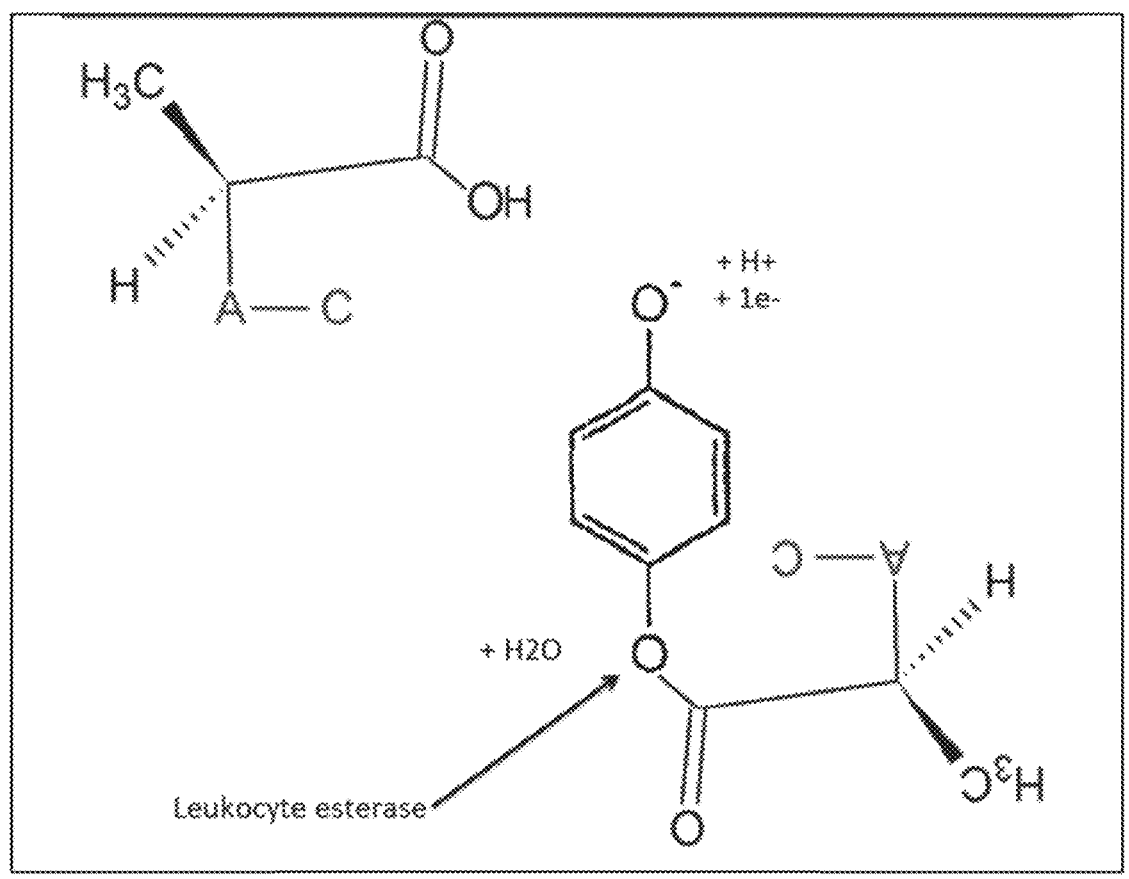
FIG. 2 represents a semiquinone intermediate and second ester hydrolysis step.
Figure 3:
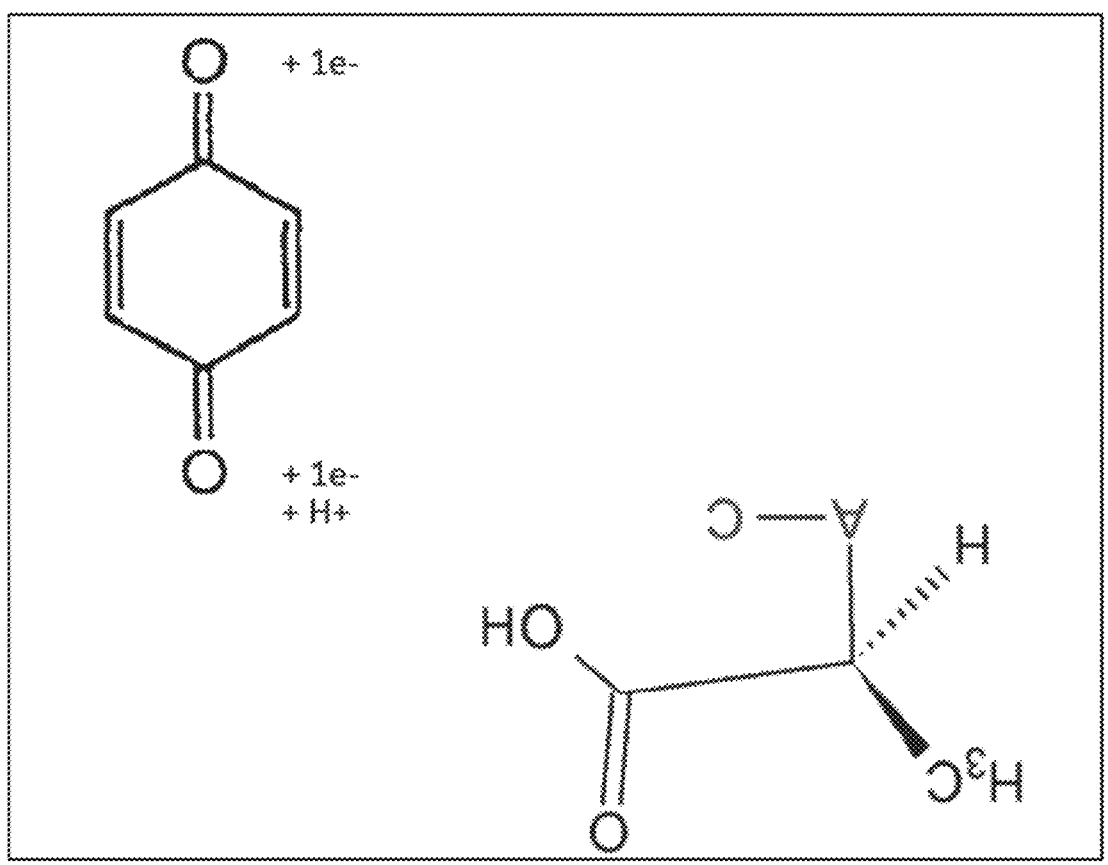
FIG. 3 represents a final benoquinone oxidation product.

In some embodiments, the redox moiety B is a derivate of phenol, which may form an ester through its hydroxyl group. Such an intermediate may undergo oxidation to release an electron. For example, but not necessarily limited to, one phenol derivative, hydroquinone, contains two hydroxyl groups in a para conformation, Each hydroxyl group can be bound to form a distinct lactate ester, which is independently a substrate of leukocyte esterase (FIG. 1). The resulting duplex substrate has two potential target sites for leukocyte esterase activity, and breakdown of the substrate is stepwise. Ester hydrolysis with leukocyte esterase at the first target will occur relatively slow due to molecular hindrance of the active sites; however, subsequent hydrolysis of the second active site will occur more quickly. This may effectively improve the specificity of an electrochemical assay, as non-specific hydrolysis would be less likely to begin the cascade. After the first ester hydrolysis step, an oxidation reaction can release an electron with removal of a hydrogen atom forming a semiquinone lactate ester intermediate (FIG. 2). After subsequent hydrolysis of the remaining ester, the quinone-based intermediate is released and can be further oxidized to form para-benzoquine. Para-benzoquine is reduced at low potentials, which minimizes interference from other redox active species within the sample and may improve assay selectivity. The final product is shown in FIG. 3.

In other aspects, methods of treating a patient with positive indication of LE and HNE is described. In one embodiment, the serious infections caused by Gram-positive bacteria are currently difficult to treat because many of these pathogens are now resistant to standard antimicrobial agents. To that end, at least one aspect of the disclosure is to prophylactically treat a patient prior to any invasive operation to minimize risk of infection. In at least one embodiment, patients identified as suffering from an infection may be initiated a comprehensive treatment plan including administering antimicrobial agent, such as penicillins, cephalosporins, tetracyclines, daptomycin, tigecycline, linezolid, quinupristin/dalfopristin and dalbavancin and the like that may be useful in combating an active infection. In other embodiments, methods of screening or detecting risk of PJI, by developing useful for the treatment of infections due to drug-resistant Gram-positives and Gram-negatives.

In some embodiments, B comprises a quinone. In some embodiments, B comprises a phenol. In some embodiments, B comprises a substituted quinone or a substituted phenol. In some embodiments, C comprises a tosyl protecting group. In some embodiments, the oxygen linking B in Formula II is substituted with an amino group. In further embodiments, B comprises aminophenyl. In some embodiments, B comprises substituted aminophenyl.

Figure 5:
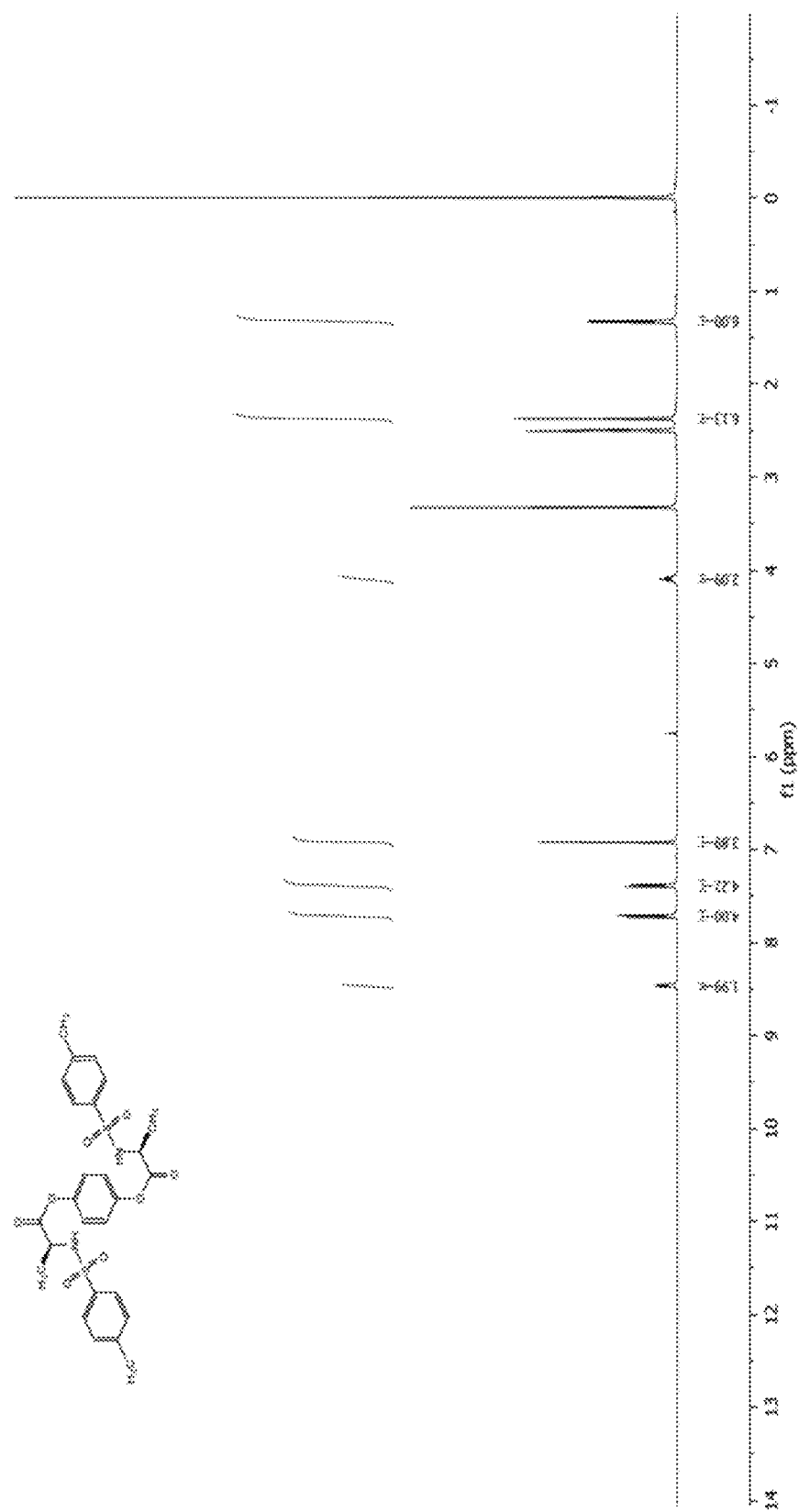
FIG. 5 represents the NMR of 4-((tosyl-L-alanyl)oxy)phenyl tosyl-L-alaninate ("TAPTA").

Two specific, explicitly non-limiting examples of substrates for detecting leukocyte esterase ("LE") that are within the scope of Formula I include 4-((tosyl-L-alanyl)oxy)phenyl tosyl-L-alaninate (Compound A below) and 4-(((S)-2-(tosyloxy)propanoyl)oxy)phenyl (S)-2-(tosyloxy)propanoate (Compound B below). Compound A is also referred to herein as "TAPTA." An NMR of Compound A is shown in FIG. 5, illustrating the tosyl moiety structure and its attachment. Phenylethylenediamine variants of Compound A and Compound B (i.e. the para-oxygens are replaced with NI linkers) are also to be considered within the scope of the present disclosure and are likewise suitable for inclusion in electrochemical assays of the present disclosure (e.g. in ICECEA).

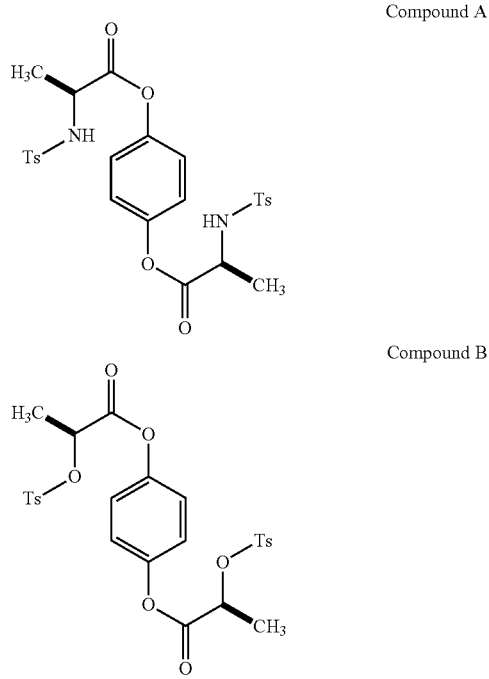

Compound A

Compound B

In some embodiments, the LE substrate comprises a composition as described in Formula II below:

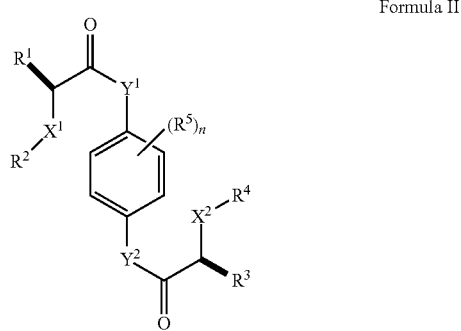

Formula II $X^1$ and $X^2$ are independently O, S or $NR^a$. $R^a$ is an H, an alkyl or an aryl group. $X^1$ and $X^2$ can be both oxygen or both $NR^a$. Alternatively, one of $X^1$ and $X^2$ is oxygen and the other is $NR^a$.

$Y^1$ and $Y^2$ are independently O, S or $NR^a$. $R^a$ is as described above. $Y^1$ and $Y^2$ can be both oxygen or both $NR^a$. Alternatively, one of $Y^1$ and $Y^2$ is oxygen and the other is $NR^a$.

$R^1$ and $R^2$ are independently an alkyl or an aryl group or a substituted alkyl, a substituted aryl or a protecting group. In some embodiments, $R^1$ or $R^2$ or both is methyl. In some embodiments, $R^1$ or $R^2$ or both may be a tosyl. In one embodiment, $R^2$ is a tosyl.

$R^3$ and $R^4$ are independently an alkyl, a protecting group such as tosyl, benzoyl, benzyl, trimethylsilyl, [bis-(4-methoxyphenyl)phenylmethyl], carbobenzyloxy, tert-Butyloxycarbonyl, 9-Fluorenylmethyloxycarbonyl, or a peptide moiety. In one embodiment, $R^4$ is a tosyl. The peptide moiety can include any combination of natural and/or non-natural amino acids.

R2 and R4 may also comprise any of the following: acetyl (Ac), benzoyl (Bz), benzyl (Bn), β-methoxyethoxymethyl (MEM), dimethoxytrityl (DMT), methyoxymethyl (MOM), methoxytrityl [(4-methoxyphenyl)diphenylmethyl](MMT), p-Methoxybenzyl (PMB), methylthiomethyl, pivaloyl (Piv), tetrahydropyranyl (THP), tetrahydrofuran (THF), trityl (Tr), sily (e.g. TMS, TBDMS, TOM, TIPS), methyl, and ethoxyethyl (EE), benzyloxycarbonyl (Cbz); p-methoxybenzylcarbonyl (Moz or MeOZ), tert-butoxycarbonyl (BOC), 9-fluorenylmethyloxycarbonyl (FMOC), 3,4-Dimethoxybenzyl (DMPM), p-methoxyphenyl (PMP), tosyl (Ts), trichloroethoxycarbonyl (Troc), arylsulfonyl, or alkylsulfonyl (e.g. Nosyl and Nps). In one embodiment, protecting group can be any one of tosyl, benzoyl, benzyl, trimethylsilyl, [bis-(4-methoxyphenyl)phenylmethyl], carbobenzyloxy, tert-Butyloxycarbonyl, 9-Fluorenylmethyloxycarbonyl.

Each of the $R^5$ on the ring is independently a halogen atom; a hydroxyl group; a $C_1$-$C_6$ alkyl group; a $C_3$-$C_6$ cycloalkyl group; a $C_3$-$C_6$ cycloalkyl $C_1$-$C_6$ alkyl group; a $C_2$-$C_6$ alkenyl group; a $C_2$-$C_6$ alkynyl group; a $C_1$-$C_6$ haloalkyl group (including trifluoro $C_1$-$C_6$alkyl); a $C_2$-$C_6$ haloalkenyl group; a $C_2$-$C_6$ haloalkynyl group; a $C_3$-$C_6$ halocycloalkyl group; a $C_3$-$C_6$ halocycloalkyl $C_1$-$C_6$ alkyl group; a $C_1$-$C_6$ alkoxy group; a $C_3$-$C_6$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ alkylcarbonylamino group; a mono ($C_1$-$C_6$ alkyl)amino group; a di($C_1$-$C_6$ alkyl)amino group; a hydroxy $C_1$-$C_6$ alkyl group; a $C_1$-$C_6$ alkoxy $C_1$-$C_6$ alkyl group; a $C_1$-$C_6$ alkylthio $C_1$-$C_6$ alkyl group; a $C_1$-$C_6$ alkylsulfinyl $C_1$-$C_6$ alkyl group; a $C_1$-$C_6$ alkylsulfonyl $C_1$-$C_6$ alkyl group; a $C_1$-$C_6$ haloalkylthio $C_1$-$C_6$ alkyl group; a $C_1$-$C_6$ haloalkylsulfinyl $C_1$-$C_6$ alkyl group; a $C_1$-$C_6$ haloalkylsulfonyl $C_1$-$C_6$ alkyl group; a cyano $C_1$-$C_6$ alkyl group; a $C_1$-$C_6$ alkoxy $C_1$-$C_6$ alkoxy group; a $C_3$-$C_6$ cycloalkyl $C_1$-$C_6$ alkyloxy group; a $C_1$-$C_6$ haloalkoxy $C_1$-$C_6$ alkoxy group; a cyano $C_1$-$C_6$ alkoxy group; a $C_1$-$C_6$ acyl group; a $C_1$-$C_6$ alkoxyimino $C_1$-$C_6$ alkyl group; a carboxyl group; a $C_1$-$C_6$ alkoxycarbonyl group; a carbamoyl group; a mono ($C_1$-$C_6$ alkyl)aminocarbonyl group; a di($C_1$-$C_6$ alkyl)aminocarbonyl group; a nitro group; or a cyano group. n is 0, 1, 2, 3, or 4. In at least one embodiment, $X^1$ and $X^2$ are independently 0 or $NR^a$. $R^a$ is a H, an alkyl, an aryl, or aralkyl group. $X^1$ and $X^2$ can be both oxygen or both $NR^a$. Alternatively, one of $X^1$ and $X^2$ is oxygen and the other is $NR^a$, in yet another embodiment, $Y^1$ and $Y^2$ are independently O or $NR^a$.

In some embodiments, the substrates detect human neutrophil elastase ("HNE"). In some embodiments, the substrates for detecting HNE (i.e. "HNE substrates") may follow Formula III as depicted below:

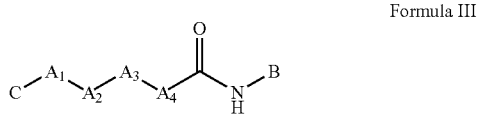

Formula III $A_1$ through $A_4$ (i.e. $A_1$-$A_2$-$A_3$-$A_4$) represent a core tetrapeptide scaffold sequence, which serves as the enzyme active site (i.e. the active site for human neutrophil elastase/HNE). A tetrapeptide sequence of Ala-Ala-Pro-Val (AAPV) (SEQ ID NO: 1) is most common, but natural or unnatural amino acids may be substituted at any of the four peptide sites in order to improve substrate sensitivity for HNE. For example, conservative substitutions may be made for SEQ ID NO: 1 and still be within the scope of the present disclosure. As used herein, "conservative substitutions" are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

B in Formula III represents a redox moiety, similar to the LE substrate displayed in Formula I above. For example, B may comprise derivate of phenol, which may form an ester through its hydroxyl group, e.g., a redox active alcohol intermediate. This may comprise, for example, a hydroquinone intermediate or hydroquinone-based redox groups. C in Formula III represents an acyl group, for example, N-methyoxysuccinyl. The acyl group may serve to improve substrate sensitivity for HNE, and some acyl groups, for example N-methoxysuccinyl, may also increase substrate solubility.

One specific, explicitly non-limiting example of a substrate for detecting HNE that is within the scope of Formula II includes 3-{[(1S)-1-{[(2S)-1-(5-{[(1S)-1-({4-[(2S)-2-({1-[(2S)-2-[(2S)-2-(3-carboxypropanamido)propanamido]propanoyl]pyrrolidin-2-yl}formamido)-3-methylbutanamido]phenyl}carbamoyl)-2-methylpropyl]carbamoyl}imidazolidin-1-yl)-1-oxopropan-2-yl]carbamoyl}ethyl]carbamoyl}propanoic acid, Compound C below.

As described above in connection with the embodiments of FIGS. 1 and 2, and Formulas II and III, there was reason to believe that a diester (consisting of two symmetric or asymmetric α-amino or α-hydroxy acid esters) would be a more effective substrate as the resulting duplex substrate would have two potential target sites for cleavage by leukocyte esterases. Further, the breakdown of the substrate would likely be stepwise such that ester hydrolysis with leukocyte esterase at the first active site would be slower, or more deliberate, due to the steric hindrance caused by the dual substrates. The initial though was that this may improve the specificity of an electrochemical assay, as non-specific hydrolysis would be less likely to begin the cascade of stepwise hydrolysis. However, Applicants found, surprisingly, that the diester was less effective than the monoester. Even in mixtures of diester and monoester in which the monoester was present in very low concentration (e.g. about 1%), the effectiveness of the monoester was predominant and dictated the effectiveness of the composition as a whole. Indeed, the effectiveness of the monoester was not discovered until the diester composition was purified to the point that the concentration of the monoester fell to below 1%. At that point, the effectiveness of the diester composition dropped precipitously, thereby indicating that the monoester was a more effective substrate for reacting with leukocyte esterase enzymes.

Accordingly, in one embodiment, the substrate of the present invention comprises a monoester, the monoester being one of an α-amino acid ester, such as an alanine ester, or an α-hydroxy acid ester, such as a lactate ester, with specificity for leukocyte esterases. The monoester has a first moiety for participating in a redox reaction, and a second moiety comprising an amine or alcohol blocking group.

In one embodiment, the composition comprises a monoester as depicted in Formula 1, wherein A comprises oxygen (O) or NR where $R^a$ is a H or an optionally substituted alkyl, aryl, or aralkyl group, whereby A determines the identity of the acyl group of the ester, in that A is O if said monoester is an α-hydroxy acid ester (i.e. lactate ester) or A is $NR^a$ if said monoester is an α-amino acid ester (i.e. alanine ester). B is the first moiety and C is the second moiety.

In one embodiment, any oxygen linking group linking the first and/or second moiety can be substituted by nitrogen linking groups, and nitrogen linking groups can be substituted by oxygen linking groups.

In one embodiment, the first moiety (B) comprises one of a substituted or unsubstituted derivative of phenol, substituted or unsubstituted hydroxyanthracene, substituted or unsubstituted aminophenol, or substituted or unsubstituted hydroxyphenanthroline.

Compound C

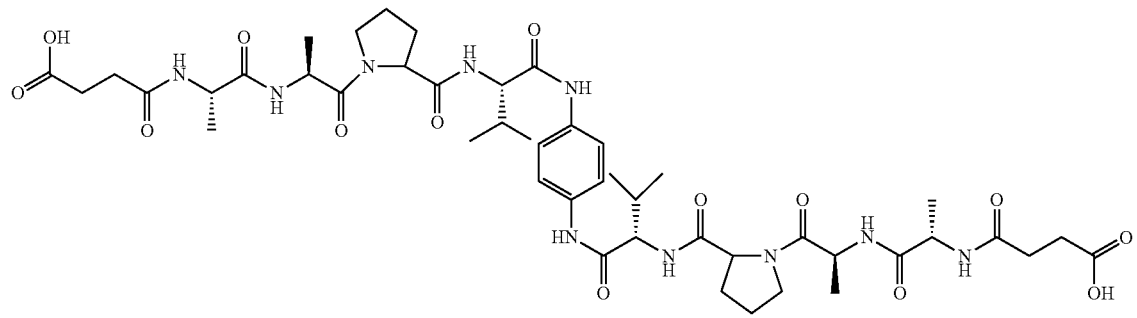

In one embodiment, the second moiety (C) comprises one of the following: acetyl (Ac), benzoyl (Bz), benzyl (Bn), β-methoxyethoxymethyl (MEM), dimethoxytrityl (DMT), methyoxymethyl (MOM), methoxytrityl [(4-methoxyphenyl)diphenylmethyl](MMT), p-Methoxybenzyl (PMB), methylthiomethyl, pivaloyl (Piv), tetrahydropyranyl (THP), tetrahydrofuran (THF), trityl (Tr), sily (e.g. TMS, TBDMS, TOM, TIPS), methyl, and ethoxyethyl (EE), benzyloxycarbonyl (Cbz); p-methoxybenzylcarbonyl (Moz or MeOZ), tert-butoxycarbonyl (BOC), 9-fluorenylmethyloxycarbonyl (FMOC). 3,4-Dimethoxybenzyl(DMPM), p-methoxyphenyl (PMP), tosyl (Ts), trichloroethoxycarbonyl (Troc), arylsulfonyl, or alkylsulfonyl (e.g. Nosyl and Nps).

In one embodiment, the second moiety is a sulfonyl group with a substituted or unsubstituted heterocycle or heteroaryl ring.

In one embodiment, Formula 1 is further refined to the general structure depicted in Formula IV:

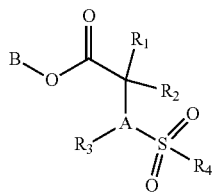

Formula IV wherein the first moiety B comprises 4-hydroxyphenyl

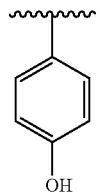

A comprises oxygen or NR$^a$, where R$^a$ is a H or an optionally substituted alkyl, aryl, or aralkyl group, whereby A determines the identity of the acyl group of the ester, R1, R2, and R3 are independently hydrogen or optionally substituted alkyl groups (R3 is absent if A is oxygen), and R4 is a substituted or unsubstituted heterocycle or heteroaryl.

In one embodiment, R4 is one of pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isooxazolyl, thiazolyl, oxazolyl, isothiazolyl, pyrrolyl, indolyl, benimidazolyl, benzofuranyl, cinnolinyl, indazolyl, indolizinyl, phthalazinyl, triazinyl, thiadiazolyl, oxadiazolyl, purinyl, 1-oxoisoindolyl, 1,2,4-trizainyl, 1,3,4-triazinyl, isoindolyl, furazanyl, benzofurazanyl, benzothiophenyl, benzotriazolyl, benzothiazolyl, benzooxazolyl, tetrahydroquinolyl, dihydroquinolyl, naphthyridinyl, quinoxalinyl, quinazolinyl, dihydroisoquinolyl, tetrahydroisoquinolyi, benzofuryl, furopyridinyl, pyrrolopyridimidinyl, or azaindolyl.

In one embodiment, R4 is a pyridine with or without the addition of substituted or unsubstituted polar groups.

In one embodiment, R4 is a pyridine selected from one of the following: pyridine (I), methoxypyridine (II), and (methoxycarbonyl)pyridine (III) as represented below:

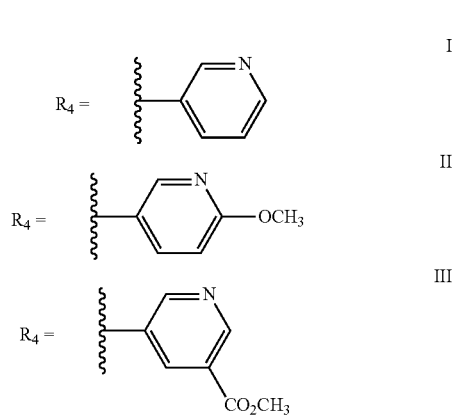

In one particular embodiment, R4 is (methoxycarbonyl)pyridine (III).

In a particular embodiment, the composition of the monoester substrate is 4-Hydroxyphenyl (N-(3-(methoxycarbonyl)pyridine-5-sulfonyl)-L-alaninate.

In yet another particular embodiment, the composition of the monoester is depicted in Formula V:

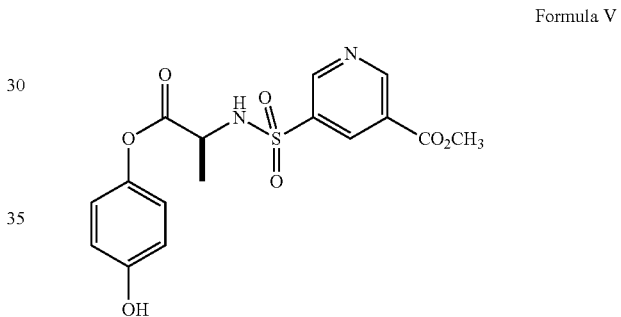

Formula V

Figure 6:
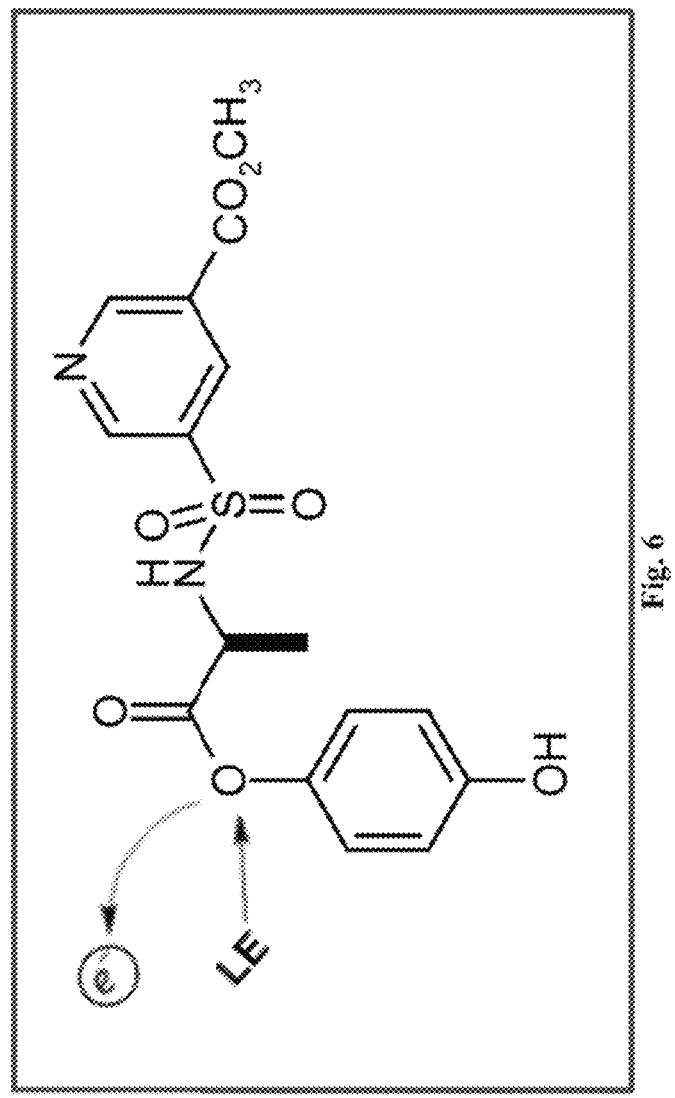
FIG. 6 is a schematic of the cleavage mechanism of a monoester embodiment of the present invention.

Referring to FIG. 6, the cleaving mechanism for Formula V is shown. Specifically, the leukocyte esterase (LE) cleaves the monoester substrate at the oxygen site upon ester hydrolysis.

In one embodiment, the substrate of the leukocyte esterase enzyme is screen-printed onto the surfaces of an electrode sensor strips using known and commercially-available techniques and materials.

As described herein, leukocytes are capable of producing leukocyte enzymes that are able to be detected and/or quantified by the electrochemical assays (i.e. ICECEA) of the present disclosure.

Leukocyte enzymes may include, for example, those described in WO 2010/036930, hereby incorporated by reference in its entirety, such as, for example, IL-1β, leukocyte elastase, leukocyte esterase, and/or gelatinase B, along with human neutrophil elastase. Leukocyte esterase ("LE") is an esterase produced by leukocytes (white blood cells). LE is the subject of, for example, urine tests for the presence of leukocytes/WBCs and other abnormalities associated with infection. Human neutrophil elastase ("HNE"), also known as human leukocyte elastase ("HLE"), is a serine protease. It is in the same family as chymotrypsin and possesses broad substrate activity. HNE is secreted by neutrophils and macrophages, two of the five classes of leukocytes as described herein. HNE is 218 amino acids long and has two asparagine-linked carbohydrate chains. There are two forms of HNE, deemed IIa and IIb.

The term "sample" as used herein may refer to a biological sample, including a sample of biological tissue or fluid origin obtained in vivo or in vitro. Biological samples can be, but are not limited to, body fluid (e.g., serous fluid, blood, blood plasma, serum, or urine), organs, tissues, fractions, and cells isolated from mammals including, for example, humans. Biological samples also may include sections of the biological sample including tissues. Biological samples may also include extracts from a biological sample, for example, a biological fluid (e.g., blood, serum, peritoneal fluid, and/or urine). Of particular interest, but explicitly non-limiting, are urine, sputum (for example, in a patient diagnosed with cystic fibrosis), peritoneal fluid (for example, in a patient with liver cirrhosis and ascites) and other serous fluids, including but not limited to, for example, synovial fluid, pleural fluid, pericardial fluid, cerebrospinal fluid ("CSF") and middle ear fluid.

In some embodiments, the presence of leukocytes, i.e. as determined by detecting and/or quantifying the amount of a leukocyte enzyme (e.g. LE and/or HNE) present in the biological sample may indicate the presence of an infection in a subject. Such embodiments may utilize the LE and/or HNE substrates of the present disclosure in an electrochemical assay, in particular ICECEA as described herein. For example, the presence of LE and/or HNE in urine may indicate a subject as having a urinary tract infection ("UTI"). Similarly, the presence of LE and/or HNE in synovial fluid may indicate a subject as having a joint infection, for example but not necessarily limited to a periprosthetic joint infection ("PJI"). These examples of indicating the presence of infection are not limited as such, as these are merely exemplary uses of the substrates of the present disclosure, and they may or may not be utilized in an electrochemical assay, for example, in an ICECEA.

In some embodiments, the substrates of the present disclosure are used to indicate a subject as having periprosthetic joint infection (PJI). PJI is a devastating complication following total joint arthroplasty, which remains a challenge for surgeons both diagnostically and therapeutically. Establishing an accurate and timely diagnosis of PJI is of critical importance for making treatment decisions. For patients presenting with a painful prosthesis, it is important to complete a work-up to either rule out or diagnose the presence of infection. In most cases, serological testing, including erythrocyte sedimentation rate (ESR) and C-reactive protein (CRP), is the initial screening test of choice. In patients with elevated serological markers or even just a high suspicion of infection, the next step is to perform joint aspiration for testing of synovial fluid. Classically, bacterial culture of synovial fluid has been used to make the diagnosis of PJI. As bacterial culture is not in itself sufficiently sensitive, with as many as 30% of infections being culture negative, orthopedic surgeons also consider the results of serological testing, synovial fluid white blood cell count and polymorphonuclear percentage, and histological analysis to make a diagnosis. Unfortunately, bacterial culture and traditional synovial fluid testing can require days to more than a week to yield a result.

Thus, in some embodiments, synovial fluid aspirated from a painful joint would be tested for LE and/or HNE activity using an enzyme substrate of the present disclosure. For example, this may be accomplished through use of an ICECEA assay as described herein. In such embodiments, the activity of LE and/or HNE would be reported as a continuous measurement of absolute concentration. This could be performed in the office or operating room to yield a result in minutes for point-of-care decision-making.

Based on an accumulation of population data, the level of LE and/or HNE activity can be combined with additional metrics to predict the likelihood that an infection is present. Additional metrics may include the type of joint, a history of prior infection, and the results of serological testing (ESR and CRP). Surgeons can consider the likelihood that an infection is present to determine the most appropriate treatment algorithm for their patient. In cases with a high likelihood that infection is present, treatment for PJI, such as prosthesis extraction and antibiotic spacer placement, incision and debridement, or long-term antibiotic suppression, could be considered based on the acuity of the infection, among other factors. In cases in which there is a moderate likelihood that infection is present, a surgeon could consider initiating treatment or waiting for additional diagnostic results. Finally, other etiologies for a painful prosthesis may be considered in cases for which the likelihood of the presence of infection is low or for which infection has largely been ruled out.

In addition to making an initial diagnosis of infection, the substrates of the current disclosure, e.g. as used in an assay (such as, for example, an ICECEA) may be used to establish the resolution of PJI in order to determine the correct timing for re-implantation of a new prosthesis. The level of LE and/or HNE activity may be used in addition to serological markers and other synovial fluid tests to determine the success of treatment, such as discussed supra. For patients with a persistently elevated LE and/or HNE, surgeons may elect to continue intravenous antibiotics or attempt an exchange of the antibiotic spacer to improve prospects of complete resolution of infection.

In some embodiments, the substrates of the present disclosure are used to indicate a subject as having spontaneous bacterial peritonitis (SBP). SBP is a serious and life-threatening complication that is relativity common in patients with liver cirrhosis and ascites. For patients with this complication, a rapid diagnosis and early administration of antibiotics is critical for survival, and in-hospital mortality can be as high as 20%. For patients with ascites, presenting symptoms of fever, change in mental status, and abdominal tenderness are frequent signs of SBP. In such cases, a diagnostic paracentesis is performed, and a diagnosis is made based on an absolute neutrophil count above 250 cells/m and/or bacterial culture.

Thus, in some embodiments, ascitic fluid obtained from diagnostic paracentesis would be tested for LE and/or HNE activity using an enzyme substrate of the present disclosure. For example, this may be accomplished through use of an ICECEA assay as described herein. Using an ICECEA assay, the activity of LE or HNE would be reported as a continuous measurement of absolute concentration. Based on an accumulation of population data collected from many patients, the absolute concentration of LE and/or HNE would be compared to gold standard diagnostic criteria to provide a calculation of the probability that SBP is present. The likelihood of infection can be used to inform the treating physician as to the most appropriate treatment algorithm. The measured level of LE or HNE could also provide important prognostic information, with a higher level indicating a worse prognosis.

In some embodiments, the substrates of the present disclosure are used to indicate a subject as having a urinary tract infection (UTI), also known as a urogenital infection. For healthy women with classic UTI symptoms, such as dysuria and frequency, and no vaginal discharge or irritation, a diagnosis of UTI can typically be made on clinical symptoms alone. On the contrary, women with poorly defined symptoms, asymptomatic pregnant females, elderly patients, and children have a much lower pre-test probability for UTI. The present disclosure is not limited to testing women for UTI. The gold standard for diagnosis of UTI is mid-stream urine culture (with $>10^1$-$10^5$ organisms) or pyuria (greater than $10^4$ leukocytes per ml).

Thus, in some embodiments, mid-stream urine for symptomatic patients would be tested for leukocyte esterase ("LE") and/or human neutrophil elastase ("HNE") activity using an enzyme substrate of the present disclosure. For example, this may be accomplished through use of an ICECEA assay as described herein. Based on population data, likelihood of infection can be determined based on both measurement of LE and/or HNE activity and additional factors, such as the presence of specific symptoms and patient characteristics (i.e. age, gender, pregnancy). Depending on the likelihood of infection, a physician can decide whether or not to administer oral antibiotics.

Population data for the clinical applications of the present disclosure (i.e. in indicating a patient as having an infection, for example, but not limited to, PJI, SBP, and/or UTI) can be used to convert the measure of LE and/or HNE activity to a predictive probability for the presence of infection. The test device itself can be used as a medium to both collect and distribute such population-based data. For example, a smartphone (or similar device) connected electrochemical biosensor can allow physicians to provide selected information to a centralized database, which may then be used to continuously improve the calculation of infection likelihood. The biosensor may also report back to surgeons the likelihood of infection for their individual patient based upon LE and/or HNE activity and additional metrics that can be used to hone their treatment algorithm.

In some embodiments, the substrates for detecting leukocyte enzymes, e.g. LE and/or HNE substrates, are incorporated into an assay. Such an assay may comprise, for example, an electrochemical assay. Electrochemical assays are cost-effective, highly sensitive, and simplify the calibration process. Furthermore, such methods would be just as effective in bloody or turbid fluid. A preferred electrochemical assay comprises an internally calibrated electrochemical continuous enzyme assay ("ICECEA"). Use of a LE substrate of the present disclosure ("TAPTA") in an ICECEA is described in Example 1, infra. ICECEAs are generally disclosed in PCT/US2014/03713 and U.S. 2016/0040209, the disclosure of which is hereby incorporated in its entirety. ICECEA utilizes integration of an enzyme-free pre-assay calibration with an electrochemical enzyme assay in a continuous experiment. This is believed to result in a uniquely shaped amperometric trace that allows for selective and sensitive determination of enzymes, e.g. LE and HNE, present in a sample.

ICECEAs generally follow the following method as described in U.S. 201610040209. First, an enzyme substrate (e.g. an LE and/or HNE substrate of the present disclosure) is placed in a background electrolyte. Next, a reactant or product of an enzymatic reaction of the enzyme is added to the first enzyme substrate/background electrolyte, which creates what is described as a "first assay mixture." Current flowing through an electrode of the electrochemical assay is then measured after the first assay mixture is formed. Next, the enzyme (e.g. LE and/or HNE) is added to the "first assay mixture" to create a "second assay mixture," and the current is measured again over a predetermined time period. Enzyme activity is determined based on the change in current over time caused by the addition of the enzyme. While optimally the enzyme is added after the reactant/product is added to the enzyme substrate, the order can be switched, i.e. the enzyme is added to the substrate first and then the reactant/product is added.

The ICECEA includes an electrochemical measuring device. The electrochemical measuring device includes a working electrode, a reference electrode, and an auxiliary electrode. The current is measured through the working electrode. The working electrode may be a noble metal electrode, metal oxide electrode, an electrode made of a carbon allotrope, or a modified electrode. The auxiliary electrode may be a platinum wire. The reference electrode may be Ag/AgCl/NaCl or any other reference electrode. The electrochemical assay system can also be made of only a working electrode and a reference electrode. Measuring the changes in current may be done by collecting an amperometric trace of the current.

Generally, in an ICECEA, adding the reactant/product to the enzyme substrate (in electrolyte) in the electrochemical assay system includes the following steps. First, a first aliquot of the reactant/product is added to the enzyme substrate (in electrolyte). Current flowing through an electrode of the electrochemical assay system is measured after the first aliquot is added. One or more additional aliquots of the reactant/product are added to the mixture and current flowing through an electrode of the electrochemical assay system is measured again. Preferably, at least three aliquots of the reactant/product are added to the enzyme substrate (in electrolyte) before the enzyme is added to the mixture. Alternatively, the aliquots of the reactant/product are added to the substrate (in electrolyte) after the enzyme is added to the mixture.

The enzymatic activity of the enzyme may be determined from the slope of a line created from measuring the current flowing through a working electrode of the electrochemical assay system after the reactant/product is added to the substrate (before the enzyme is added, or vice versa as described herein) at predetermined intervals over a predetermined time period. An advantage of this method is that the addition of the reactant/product to the substrate (in electrolyte) and the addition of the enzyme are performed in the same container using the same electrode.

In at least one embodiment, a customized kit is described containing a solution of enzyme substrate and other necessary reactants in a background electrolyte; a solution of redox active component of enzymatic reaction; and a solution of assayed enzyme. As such, an amperometric measurement is done by using any electrochemical measurement device with amperometric method and a conventional electrochemical cell with the working, reference, and counter electrodes immersed in a solution containing the enzyme substrate. The working electrode is held at a potential E vs. the potential of the reference electrode. The potential E is adequate for either the oxidation or reduction of species present in the solution containing the redox active component of the enzymatic reaction. The experiment is performed by spiking one or more known aliquots of a redox active containing solution followed by one aliquot of a solution containing assayed enzyme into a stirred solution that contains enzyme substrate and other necessary reactants and measuring the current flowing through the working electrode.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference in their entireties.

Publications disclosed herein are provided solely for their disclosure prior to the filing date of the present invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, as well as each document or reference cited in each of the herein-cited references (including any manufacturer's specifications, instructions, etc.), is hereby expressly incorporated herein by reference.

The following non-limiting examples serve to further illustrate the present disclosure.

VI. EXAMPLES

1. Use of 4-((tosyl-L-alanyl)oxy)phenyl tosyl-L-alaninate in an Internally Calibrated Electrochemical Continuous Enzyme Assay (ICECEA)

Figure 4:
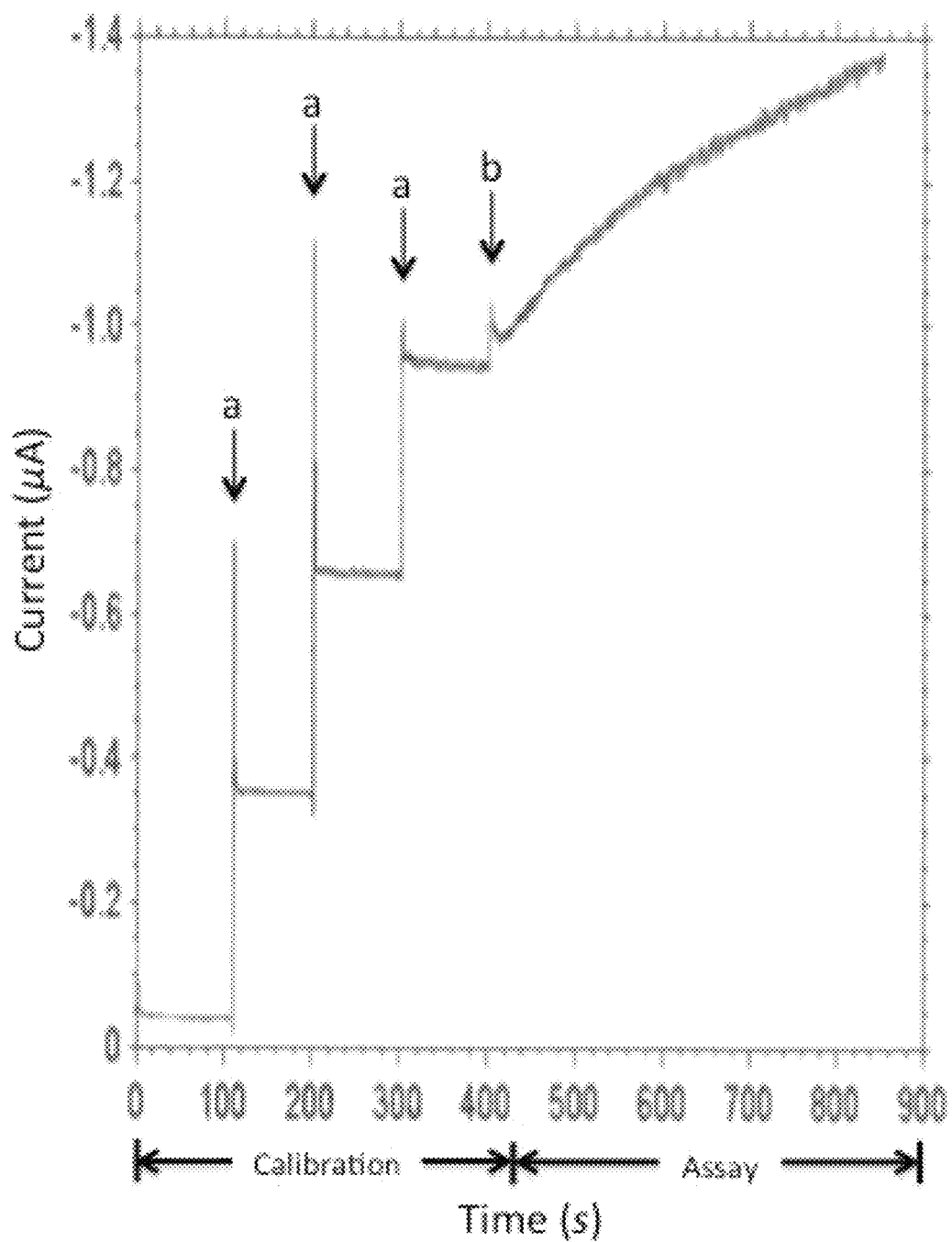
FIG. 4 represents the results of using 4-((tosyl-L-alany)oxy)phenyl tosyl-L-alaninate ("TAPTA") in an internally calibrated electrochemical continuous enzyme assay (ICECEA).

The substrate 4-((tosyl-L-alanyl)oxy)phenyl tosyl-L-alaninate, Compound A below (also referred to as "TAPTA") was used as a substrate to measure the activity of leukocyte esterase (LE) in an internally calibrated electrochemical continuous enzyme assay (ICECEA). The results are indicated in FIG. 4.

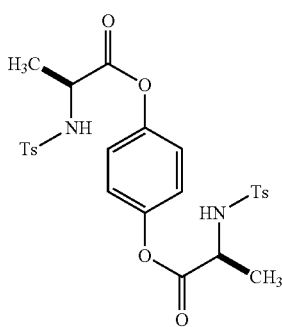

Compound A

The ICECEA was conducted as generally described in U.S. 2016/0040209 as well as in the detailed description supra. Briefly, in the pre-assay phase, three (3) distinct calibration steps were performed by spiking a solution of enzyme substrate ("TAPTA") and necessary reactants with a solution of the redox active component of the enzymatic reaction. These three distinct calibration steps are denoted by a bold "a" in FIG. 4. After calibration, the assay phase was commenced by spiking one aliquot of assayed enzyme (LE) into the enzyme substrate solution. This step is denoted by a bold "b" in FIG. 4. The enzymatic reaction was followed by measuring current flowing through the working electrode. The enzyme assay was calibrated for LE concentrations ranging from 0-250 µg/L. The enzyme activity of LE demonstrated a linear response relative to LE concentration and predictive of an infection.

2. Synthesis of Monoester of Formula V

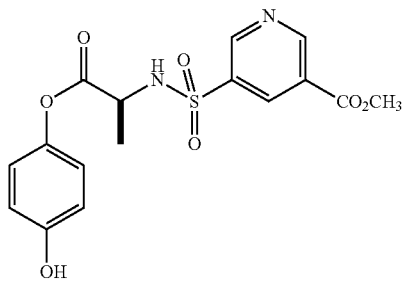 [SMILES: COC(=O)c1cncc(S(=O)(=O)N[C@@H](C)C(=O)Oc2ccc(O)cc2)c1]

Example 2a

4-Hydroxyphenyl (N-(3-(methoxycarbonyl)pyridine-5-sulfonyl)-L-alaninate (Monoester) can be prepared by partial hydrolysis of 1,4-Phenylene bis(N-(3-(methoxycarbonyl)pyridine-5-sulfonyl)-L-alanininate (synthesized by a modification of the procedure for Compound III described in Hanson et al., Chembiochem 2018, 19, https://www.ncbi.nlm.nih.gov/pubmed29679431). Suitable bases include alkali hydroxides, alkaline earth hydroxides, ammonia, amines, etc.

Example 2b. Hydrolysis with NaOH 1,4-Phenylene bis(N-(3-(methoxycarbonyl)pyridine-5-sulfonyl)-L-alanininate (21 mg, 0.032 mmol) was dissolved in THF and treated with 1M NaOH (0.045 mL, 139 mol %), at 30° C. for 4 days. The solvent was evaporated, the residue was dissolved in dichloromethane, rinsed with 1M HCl, and dried over $MgSO_4$ to give the product as a colorless glass.

Example 2c. Hydrolysis with Triethylamine 1,4-Phenylene bis(N-(3-(methoxycarbonyl)pyridine-5-sulfonyl)-L-alanininate (98 mg, 0.151 mmol) was dissolved in dichloromethane (2 mL) and triethylamine (28 mg, 0.277 mmol, 184 mol %). Water (62 mg) was added and the heterogeneous mixture was stirred at 30° C. for 3 days. 1M HC was added to pH 1. The layers were separated, and the aqueous layer was extracted twice with dichloromethane. The combined organic extracts were dried over $MgSO_4$ and evaporated to give a pink foam. Chromatography on silica gel with dichloromethane-ethyl acetate (70:30) afforded 4-Hydroxyphenyl (N-(3-(methoxycarbonyl)pyridine-5-sulfonyl)-L-alaninate (36 mg, 63% yield) as a white crystalline solid, mp 113-116° C. NMR (DMSO-$d_6$) δ 1.37 (3H, d), 3.91 (3H, s), 4.31 (1H, q), 6.68 (4H, Abq), 8.59 (1H, t), 8.96 (1H, br), 9.18 (1H, d), 9.22 (1H, d), 9.47 (1H, s); $ms^+$ 381 $(M+H)^+$; $ms^-$ 379 $(M-H)^-$.

Example 2d. Synthesis of 4-Hydroxyphenyl (N-(3-(methoxycarbonyl)pyridine-5-sulfonyl)-L-alaninate from L-Alanine Tert-Butyl Ester or L-Alanine Benzyl Ester L-Alanine tert-butyl ester was condensed with methyl 5-(chlorosulfonyl)pyridine-3-carboxylate in the presence of triethylamine. The tert-butyl group was removed by treatment with HCl (g) in dichloromethane to give N-(3-(methoxycarbonyl)pyridine-5-sulfonyl)-L-alanine. This intermediate was also prepared by condensation of L-alanine benzyl ester with methyl 5-(chlorosulfonyl)pyridine-3-carboxylate followed by hydrogenation in EtOAc over Pd/C. N-(3-(methoxycarbonyl)pyridine-5-sulfonyl)-L-alanine was condensed with excess hydroquinone in acetonitrile in the presence of DCC and DMAP to afford Hydroxyphenyl (N-(3-(methoxycarbonyl)pyridine-5-sulfonyl)-L-alaninate. Alternatively, N-(3-(methoxycarbonyl)pyridine-5-sulfonyl)-L-alanine was condensed with hydroquinone monobenzyl ether or mono-BOC-hydroquinone [tert-butyl 4-(hydroxyphenyl) carbonate] followed by hydrogenation over palladium in acetic acid or hydrolysis with HCl (g) respectively to afford 4-Hydroxyphenyl (N-(3-(methoxycarbonyl)pyridine-5-sulfonyl)-L-alaninate.

Figure 7:
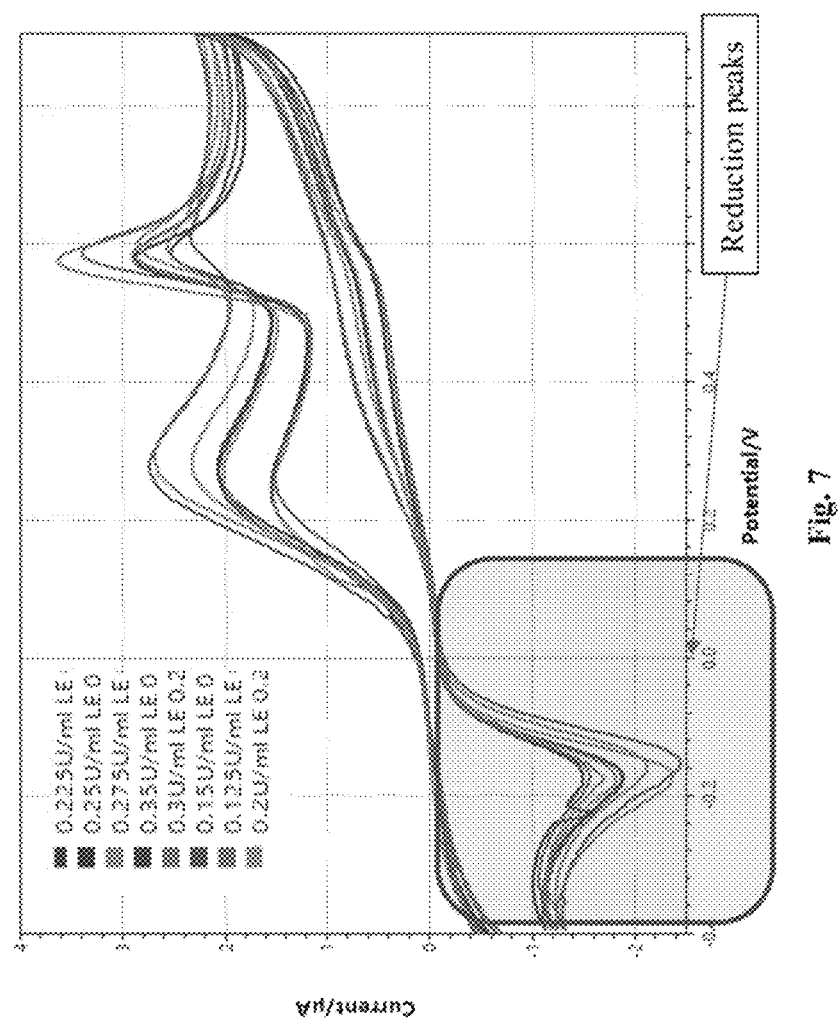
FIG. 7 are voltammograms showing increasing reduction peaks with higher LE concentration for an electrode screen-printed with one embodiment of a substrate of the present invention.

3. Use of 4-Hydroxyphenyl (N-(3-(methoxycarbonyl)pyridine-5-sufoyl)-L-alaninate on Screen-Printed Electrode Referring to FIG. 7, the effectiveness of using the substrate of the present invention on a screen-printed electrode strip is demonstrated. Specifically, electrode strips were screen printed with the substrate having the structure as depicted in Formula V. The strips were contacted with varying concentrations of LE (i.e. 0.125 U/m to 0.35 U/ml LE).

The plot clearly indicates significant reduction peaks at about −0.17 V, which correspond to the redox reaction of hydroquinone molecules that are released upon cleavage of the monoester by leukocyte esterases at the ester active site. Moreover, because the reduction peaks were seen to be directly related to the LE activity within the sample in a dose dependent manner, the screen-printed electrode strips not only were confirmed to detect the presence of LE, but also can provide a quantitative measure as to the activity level or concentration of LE in a sample that directly corresponds to the enzymes cleavage of the monoester. Based on this measured level, a determination can be made as to whether the patient's level of LE is high enough to indicate infection.

The foregoing examples and description of the preferred embodiments should be taken as illustrating, rather than as limiting the present disclosure as defined by the claims. As will be readily appreciated, numerous variations and combinations of the features set forth above can be utilized without departing from the present disclosure as set forth in the claims. Such variations are not regarded as a departure from the scope of the disclosure, and all such variations are intended to be included within the scope of the following.

What is claimed is:
1. A substrate composition for leukocyte esterases comprising a monoester, wherein said monoester is 4-Hydroxyphenyl (N-(3-(methoxycarbonyl)pyridine-5-sulfonyl)-L-alaninate.
2. A substrate composition for leukocyte esterases comprising a monoester, wherein said monoester is represented by the following structure of Formula V.

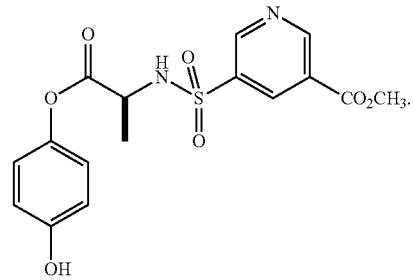

Formula V

3. An electrochemical device for detecting leukocyte esterases comprising a substrate with the composition of claim 2.
4. The electrochemical device of claim 3, wherein said composition is screen printed onto an electrode sensor.
5. A method of screening a patient at risk of infection comprising detecting the presence of a leukocyte esterase enzyme in an electrochemical assay comprising the steps:
 applying or contacting a biological sample to an electrode sensor strip, said electrode sensor strip comprising the composition of claim 2;
 measuring current or voltage flowing through said electrode sensor strip using a potentiometric or voltammetric reader; and
 determining a level of activity of leukocyte esterases based on said current or voltage, wherein said level of activity is indicative of an infection.
6. The method of any of claim 5, wherein the biological sample comprises one of urine, sputum, synovial fluid, peritoneal fluid, pleural fluid, pericardial fluid, cerebrospinal fluid, gastric fluid, amniotic fluid, and middle ear fluid.
7. The method of any of claim 5, wherein said level of activity indicates the presence of activated leukocytes in said sample, which is indicative of an infection.
8. The method of claim 7, wherein said infection comprises one of periprosthetic joint infection (PJI), native joint infection, urinary tract infection (UTI), bacterial peritonitis, meningitis, and endometritis.

\* \* \* \* \*